United States Patent [19]

Keith et al.

[11] Patent Number: 5,679,339

[45] Date of Patent: Oct. 21, 1997

[54] METHOD OF USING IL-11 FOR TREATING SPONDYLOARTHROPIES

[76] Inventors: James Keith, 28 Vine St., Andover, Mass. 01810; Paul Schendel, 39 Jeffrey Rd., Wayland, Mass. 01778

[21] Appl. No.: 495,724

[22] Filed: Jun. 27, 1995

[51] Int. Cl.$^6$ .............. A61K 45/05; C07K 17/00
[52] U.S. Cl. .................. 424/85.2; 530/351
[58] Field of Search ............... 530/350 T, 351; 424/85.1, 85.2

[56] References Cited

FOREIGN PATENT DOCUMENTS

WO 91/07495 A1 5/1991 WIPO.
WO 94/05318 A1 3/1994 WIPO.
WO 95/24650 A2 9/1995 WIPO.

OTHER PUBLICATIONS

Feldmann et al., Annu. Rev. Immunol., 14:397–440, 1, 1996.
Girasole et al., J. Clin. Invest., 93: 1516–1524, 5, 1994.
Paul. In: Fundamental Immunology, Editor, William E. Paul, Publisher, Raven Press, 1, 1996, New York.
Brennan, Clin. Exp. Immunol., 97: 1–3, 1, 1994.
J.P. Leonard et al., J. Exp. Med 181:381–386 (1995).
R.H. Scofield et al., PNAS 90:9330–9334 (1993).
R.E. Hammer et al., Cell 63:1099–1112 (1990).
Sonis, et al., Proceedings of the American Assoc. for Cancer Research 36:368 (1995) (abstract 2190).
Keith, Jr. et al., Gastroenterology 108(4):A846 (1995) (abstract).
Keith, Jr. et al., Gastroenterology 106(4):A708 (1994) (abstract).
Keith, Jr. et al., Stem Cells 12(S1):79–90 (1994).
Opal, et al., Blood 86(10):498A (1995) (abstract).
Sonis, et al., European Journal of Cancer, Part B, Oral Oncology 31B(4):261–266 (1995).

Primary Examiner—Christina Y. Chan
Assistant Examiner—Patrick J. Nolan
Attorney, Agent, or Firm—M. C. Meinert

[57] ABSTRACT

Provided by the present invention are methods of treating a variety of disorders including AIDS, arthritis (rheumatoid arthritis, osteoarthritis, spondyloarthropathies), antibiotic induced diarrheal diseases (*Clostridium difficile*), multiple sclerosis, osteoporosis, gingivitis, peptic ulcer disease, esophagitis, diabetes, retinitis, uveitis, reperfusion injury after myocardial infarction (MI) or cerebral vascular accident (CVA), aphthous ulcers (oral), atherosclerosis (plaque rupture), prevention of minor metastases, asthma, preeclampsia, and allergic disorders such as rhinitis, conjunctivitis, and urticaria.

2 Claims, No Drawings

METHOD OF USING IL-11 FOR TREATING SPONDYLOARTHROPIES

FIELD OF INVENTION

The present invention relates generally to methods of treating disorders such as AIDS, arthritis (rheumatoid arthritis, osteoarthritis, spondyloarthropathies), antibiotic induced diarrheal diseases (*Clostridium difficile*), multiple sclerosis, osteoporosis, gingivitis, peptic ulcer disease, esophagitis, diabetes, retinitis, uveitis, reperfusion injury after myocardial infarction (MI), cerebral vascular accident (CVA), aphthous ulcers (oral), atherosclerosis (plaque rapture), prevention of minor metastases, asthma, preeclampsia, and allergic disorders such as rhinitis, conjunctivitis, and urticaria.

BACKGROUND OF THE INVENTION

Inflammatory responses include a broad range of host reaction to a variety of insults, such as injury, infection, or rejection. It is the over production of mediators that is believed to be associated with a broad range of disorders, including AIDS, arthritis (rheumatoid arthritis, osteoarthritis, spondyloarthropathies), antibiotic induced diarrheal diseases (*Clostridium difficile*), multiple sclerosis, osteoporosis, gingivitis, peptic ulcer disease, esophagitis, diabetes, retinitis, uveitis, reperfusion injury after myocardial infarction (MI), cerebral vascular accident (CVA), aphthous ulcers (oral), atherosclerosis (plaque rupture), tumor metastases, asthma, preeclampsia, and allergic disorders such as rhinitis, conjunctivitis, and urticaria.

These disorders and their symptoms are briefly summarized below. According to the methods of the present invention, IL-11 is administered to modulate the hosts' over reaction to insult thereby treating the following disorders.

AIDS: Infection with HIV eventually leads to destruction of T-helper cells producing an immuno-compromised state. However, some immune cells, such as the macrophage may actually be stimulated during HIV infection. HIV-infected macrophages exhibit enhanced TNF-α production when the cells are stimulated. Excessive TNF-α production has been linked to increased pulmonary damage occurring during AIDS and has been linked to the cachexia(weight loss) which is characteristic of the disease.

Arthritis:

Rheumatoid Arthritis: In rheumatoid arthritis, the synovial tissue lining the joint organizes into a mass that infiltrates and degrades articular cartilage, tendons, and bone. Normal synovial tissue consists of a thin membrane of only two or three cell layers, comprised principally of fibroblast-like synovial cells and rare resident macrophages. In contrast, rheumatoid synovial tissue consists of a mixture of cell types: immune T- and B-cells, monocyte/macrophages, polymorphonuclear leucocytes, and the fibroblast-like cells with their rampant proliferative ability. With the exception of the fibroblasts, most of these cells are recruited to the rheumatoid joint in response to inflammatory stimuli that occur as part of the pathology of this disease.

Although the etiology of rheumatoid arthritis is not clear, it is suspected that an unknown antigen, such as a bacterium, virus, or mycoplasma, is deposited in the joints as a consequence of a systemic infection. Normally, the antigen is cleared and no disease arises; however, in genetically susceptible individuals, the antigen elicits an acute inflammatory/foreign body response in which some autologous tissue damage occurs. This, in turn, develops into an (auto)immune response and eventually leads to a chronic inflammatory and immunologic reaction within the synovial lining of the joint. Thus, there is a potpourri of activated cell types, and the cytokines they produce continuously fuel the proliferative and destructive ability of the synovial fibroblasts.

Osteoarthritis: In osteoarthritis, degenerative changes to the articular cartilage, subchondral bone and the synovial membrane occur after various joints are subjected to repeated mechanical damage. Increased levels of IL-1, TNF-α and metalloproteases have been documented within the affected joints of patients.

Spondyloarthropathies: The diseases classified as spondyloarthropathy are psoriatic arthritis (PsA), juvenile chronic arthritis with late pannus onset, enterogenic spondyloarthropathies (enterogenic reactive arthritis (ReA) and inflammatory bowel diseases (IBD)), urogenital spondyloarthropathies (urogenital ReA), and the undifferentiated spondyloarthropathies.

In this type of arthridity, various types of immune mediated joint inflammation produce degenerative changes in the multiple joints. These changes consist of inflammatory infiltration within the synovial membranes and degenerative changes to the articular cartilage and the associated subchondral bone. One additional feature of this particular syndrome is that of the development of bony bridges (spondyloses) between the affected joint components. Again, increased levels of IL-1, TNF-α and metalloproteases have been documented within the affected joints of patients.

Antibiotic Induced Diarrheal Diseases: Yet another inflammatory disorder is antibiotic induced diarrheal diseases (e.g., by organisms such as *Clostridium difficile*). *Clostridium difficile* is a common cause of diarrhea and colitis in individuals receiving broad spectrum antibiotic therapy. Toxins released by the bacteria elicit an enterotoxigenic secretory diarrhea and also elicit an acute inflammatory response in the intestinal mucosa characterized by granulocyte infiltration, epithelial cell necrosis, ulceration and hemorrhagic edema.

Multiple Sclerosis: Multiple sclerosis (MS) is an inflammatory demyelinating disorder of the central nervous system (CNS). MS is characterized histopathologically by focal lesions in different stages of evolution in the white matter of the CNS. Breakdown of the blood-brain barrier and inflammatory perivascular infiltration are the first events in lesion formation and are followed by demyelination and astrogliosis. Local intimation is most probably induced by an autoimmune response against the myelin sheath. Proteolytic enzymes are believed to contribute to the inflammatory tissue damage in this disease. Gelatinases, belonging to the matrix metalloproteases, contribute to tissue destruction in inflammatory demyelinating disorders of the central nervous system such as multiple sclerosis.

Clinical diagnosis of MS is based on the history and physical findings indicating multiple lesions in the CNS. Although some cases are progressive from the onset, most show remissions and exacerbations with lesions occurring in different places in the white matter. As in experimental allergic encephalomyelitis (EAE), the symptoms of MS vary from one individual to another and from one time to another in any particular patient. EAE is a T cell-mediated autoimmune disease of the CNS.

Immune abnormalities have been described in the peripheral blood and cerebrospinal fluid of MS patients, including the presence of inflammatory T-cells, increased synthesis of immunoregulatory cytokines, and oligoclonal immunoglobulin. Although the exact cause of MS is unknown, MS might be the consequence of auto-sensitization to myelin antigens, probably induced as cross-reactions to viral or bacterial proteins.

Osteoporosis: Postmenopausal osteoporosis is a disorder characterized by a progressive loss of bone tissue which begins after natural or surgical menopause and leads to the occurrence of spontaneous fractures. Although estrogen deficiency is known to cause bone loss by stimulating the resorptive activity of mature osteoclasts (OCs) and the proliferation and differentiation of OC precursors, the mechanism of these effects is still conjectural at best. One such mechanism may be a modulatory effect on the secretion of factors that are produced in the bone microenvironment and influence bone remodeling. Among these are IL-1, IL-6, and tumor necrosis factor α and β (TNF). IL-I and TNF promote bone resorption in vitro and in vivo by activating mature OCs indirectly, via a primary effect on osteoblasts, and by stimulating the proliferation and differentiation of OC precursors. IL-6 also increases OC formation from hemopoietic precursors. However, IL-6 does not activate mature OCs.

Gingivitis: Adult periodontitis is strongly associated with infection by *Porphyromonas gingivalis*. Proteolytic enzymes, which are produced in large quantity by this bacteria, are considered as important pathogenic agents. The increased production and flow of gingival crevicular fluid (GCF) is an important change in gingival tissues during periodontal infection, correlating with clinical indices of gingival intimation. Indeed, salivary protein and albumin concentrations of individuals with periodontitis, which are an indication of plasma leakage due to vascular permeability enhancement (VPE), are significantly increased compared to healthy subjects. The production of GCF appears dependent on VPE induced at periodontitis sites, presumably involving proteinase(s) of *P. gingivalis* in their generation.

Peptic Ulcer Disease: Inhibition of gastric acid secretion with $H_2$-receptor antagonists and, more recently, blockers of $H^+,K^+$-ATPase (also known as the proton pump) has been the mainstay of therapy for peptic ulcer disease. The pathophysiology of peptic ulcers remains obscure. An appreciation of the complexity of the physiology of the gastric mucosa has led to a hypothesis that peptic ulcers are the result of an imbalance in the relative importance of aggressive (acid, pepsin) and protective (mucus, bicarbonate, blood flow, prostaglandins, etc.) factors. Infection of the mucosa of the human gastric antrum with the bacterium *Helicobacter pylori* has been widely accepted as the cause of chronic, active, type B gastritis. Further, this form of gastritis has been linked directly to peptic ulcer disease by studies showing that eradication of *H. pylori* reverses this gastritis and prevents duodenal ulcer relapse. Because cytokines are the principal mediators by which immune/inflammatory cells communicate with each other and with other cells, it is likely that these small peptides are involved in the pathogenesis of chronic active type B gastritis and the resulting peptic ulcer disease.

Some cytokines (IL-1, epidermal growth factor, transforming growth factor-α, acidic and basic fibroblast growth factors) tip the balance towards peptic ulcer healing; others (tumor necrosis factor-α appear to have no effect; still others (IL-4) may even cause gastrointestinal damage.

Esophagitis: The most common cause of esophagitis is the chronic reflux of hydrochloric acid from the stomach due to inefficiency of the cardiac sphincter of the stomach. The chronic presence of acid in the lower esophagus leads to damage of the esophageal mucosa. In the most severe form, a syndrome called Barrett's esophagus can develop which often leads to esophageal cancer. Other causes of esophagitis include parenteral chemotherapy and ionizing radiation, associated with radiation therapy for cancer in the thoracic cavity.

Diabetes: Infiltration of the pancreatic islets by immune/inflammatory cells (insulitis), followed by loss of the insulin-producing beta cells is the characteristic histologic feature of insulin-dependent diabetes mellitus (IDDM).

IDDM is a T cell-mediated chronic autoimmune disease that is characterized by lymphocytic infiltration of the pancreatic islets of Langerhans and by the selective destruction of insulin-producing β cells in the islets. Since TNF-α is a proinflammatory cytokine and its gene is localized within the major histocompatibility complex (MHC), which has been shown to have a strong genetic linkage to several autoimmune disorders including IDDM, TNF-α has been considered to be a possible candidate cytokine mediating the pathogenic destruction of β-islet cells.

Retinitis: Inflammation of the light sensitive retina, retinitis, can occur due to a variety of viral, bacterial or autoimmune etiologies. The end result is destruction of the retina and loss of sight.

Uveitis: Inflammation of the anterior portion of the eye its associated structures, the iris and cornea occurs with a relatively high frequency in patients with autoimmune disorders.

Reperfusion Injury after Myocardial Infarction (MI) and Cerebral Vascular Accident (CVA): Ischemia-induced endothelial cell injury has been described as the pivotal causative event leading to an array of pathophysiologic sequelae such as microvascular vasoconstriction, adhesion and aggregation of platelets and neutrophils, and decreased blood flow, inclusively described as the "no reflow-phenomenon" early after reperfusion.

The infiltration and activation of multiple types of inflammatory cells result in a series of degenerative changes in the vasculature of the affected area, as well as inciting damage of the surrounding parenchymal tissue.

Aphthous Ulcers (oral): Although the cause of aphthous ulcers remain unknown, many physicians believe they are caused by autoimmune phenomena, which cause the destruction of discrete areas of the oral mucosa which leads to oral ulceration. Among the cytokines present in these active areas of ulceration, TNF-a appears to play a predominant role.

Age-related diseases such as atherosclerosis (plaque rupture), fibrosis, osteoporosis, and many others, are associated with increased levels of certain cytokines such as IL-1, IL-6 and TNF-α, suggesting that physiological aging in humans is associated with an increased capability of peripheral blood mononuclear cells to produce proinflammatory cytokines. Although atherosclerosis contributes to the narrowing of the blood vessel lumen, often the large atherosclerotic plaques cause fewer problems than smaller plaques. This occurs due to the sudden rupture of medium sized plaques. It appears that this rupture is associated with increased concentrations of various metalloproteases, probably derived from inflammatory cells within the plaque.

Prevention of Tumor Metastases: The processes of tumor invasion and metastasis are thought to depend upon increased proteolytic activity of invading minor cells. Matrix metalloproteinases, cathepsins B, D, and L, and plasminogen activator have been proposed to participate in the metastatic cascade. Cathepsin D has been suggested to be an independent marker of prognosis in breast cancer.

Asthma: Asthma is a disease with two major components, a marked inflammatory reaction and a disorder of bronchial smooth muscle reactivity producing bronchospasm. Increased production of inflammatory mediators causes infiltration of leukocytes, with lymphocytes, eosinophils and mast cells being present in large quantities.

Allergic Disorders such as: Rhinitis, Conjunctivitis and Urticaria ("hives"):

In these three types of intimation, multiple allergens are capable of evoking the infiltration and activation of "allergic" classes of leukocytes, i.e., eosinophils, mast cells and basophils, resulting in the subsequent release of histamine, platelet activating factor, etc. Given this general type of reaction, these aforementioned disorders occur in the nose, conjunctiva and the skin.

Preeclampsia: Preeclampsia is characterized by development of hypertension, endothelial cell disruption, coagulopathy, leukocyte activation, edema, renal dysfunction, and fetal growth disturbances after the twentieth week of pregnancy and occurs in 8% to 10% of all pregnancies in the United States annually. The endothelial cell damage seen in preeclampsia may be produced in part by TNF-α.

It has been recently reported that IL-11 is produced by placental fibroblasts and that it causes proliferation and differentiation of the trophoblast, the major cell type of the placenta. In non-pregnant individuals, IL-11 causes a physiologic plasma volume expansion which is very similar to that caused by normal pregnancy. IL-11 also appears to be able to decrease TNF-α by activated macrophages. In preeclampsia, trophoblast growth and differentiation are abnormal, plasma volume expansion fails to occur and TNF-α levels are elevated, indirectly suggesting a deficiency of IL-11.

In Graft vs. Host Disease (GVHD), the immunologic recognition and response seen are believed to be caused by histocompatibility differences between the donor and recipient and cytotoxicity by alloreactive T cells. The cellular injury in GVHD is thought to be caused by cellular infiltration of effector cells into target tissues with resultant destruction. The theory of the destruction seen in GVHD was based on the observation of lymphocytes juxtaposed to dying cells (satellitosis) observed frequently in the skin of patients or animals with GVHD. Pulmonary complications are often lethal components of acute GVHD.

BRIEF SUMMARY OF THE INVENTION

Provided by the present invention are methods of treating a variety of disorders including AIDS, arthritis (rheumatoid arthritis, osteoarthritis, spondyloarthropathies), antibiotic induced diarrheal diseases (*Clostridium difficile*), multiple sclerosis, osteoporosis, gingivitis, peptic ulcer disease, esophagitis, diabetes, retinitis, uveitis, reperfusion injury after myocardial infarction (MI) or cerebral vascular accident (CVA), aphthous ulcers (oral), atherosclerosis (plaque rupture), prevention of tumor metastases, asthma, preeclampsia, and allergic disorders such as rhinitis, conjunctivitis, and urticaria.

According to the present invention, IL-11, analogs, and derivatives thereof, are administered to patients, either prophylactically or at the onset of symptoms associated with the aforementioned disorders. IL-11 can be administered in suitable pharmaceutically acceptable carriers either alone or in combination with other conventional agents useful in alleviating the symptoms associated with the aforementioned disorders. A suitable IL-11 formulation comprises, for example, 5 mg IL-11, 3.10 mg histidine, and 22.5 mg glycine, for example, as a lyophilized powder which can be reconstituted with 1 ml sterile water for injection. IL-11 can be supplied intravenously or can be applied topically in formulations to the nasal mucosa or the conjunctiva or oral mucosa as an aqueous drop formulation or mouthwash, respectively. In localized surface reactions, a topical formulation is preferred whereas in more severe generalized body-wide inflammatory states, parental routes, such as subcutaneous or intravenous injection are preferred. Suitable doses of IL-11 are in the range of 1–50 μg/kg subcutaneous for multiple daily doses and for shorter periods of treatment in severe inflammatory states, doses are increased to 50 to 100 μg/kg subcutaneous or intravenous. Doses are administered daily for between one day and six months, or for as long as is deemed necessary and safe in the treatment of the aforementioned disorders, as is readily ascertained by standard tests by the attending physician, depending upon the nature of the disorder being treated.

DETAILED DESCRIPTION OF THE INVENTION

Provided by the present invention are methods for using IL-11 for the treatment of AIDS, arthritis (rheumatoid arthritis, osteoarthritis, spondyloarthropathies), antibiotic induced diarrheal diseases (*Clostridium difficile*), multiple sclerosis, osteoporosis, gingivitis, peptic ulcer disease, esophagitis, diabetes, retinitis, uveitis, reperfusion injury after myocardial infarction (MI), cerebral vascular accident (CVA), aphthous ulcers (oral), atherosclerosis (plaque rupture), prevention of tumor metastases, asthma, preeclampsia, and allergic disorders such as rhinitis, conjunctivitis, and urticaria.

Interleukin 11 (IL-11) is a pleiotropic cytokine that stimulates primitive lymphohematopoietic progenitor cells and synergizes with other hematopoietic growth factors to stimulate the proliferation and maturation of megakaryocytes. IL-11 is described in detail in International Application PCT/US90/06803, published May 30, 1991; as well as in U.S. Pat. No. 5,215,895; issued Jun. 1, 1993. A cloned human IL-11 was previously deposited with the ATCC, 12301 Parklawn Drive, Rockville, Md., on Mar. 30, 1990 under ATCC No. 68284. Moreover, as described in U.S. Pat. No. 5,270,181; issued Dec. 14, 1993; and U.S. Pat. No. 5,292,646; issued Mar. 8, 1994; IL-11 may also be produced recombinantly as a fusion protein with another protein. IL-11 can be produced in a variety of host cells by resort to now conventional genetic engineering techniques. In addition, IL-11 can be obtained from various cell lines, for example, the human lung fibroblast cell line, MRC-5 (ATCC Accession No. CCL 171) and Paul et al., the human trophoblastic cell line, TPA30-1 (ATCC Accession No. CRL 1583). Described in Proc Natl Acad Sci USA 87:7512 (1990) is a cDNA encoding human IL-11 as well as the deduced amino acid sequence (amino acids 1 to 199). U.S. Pat. No. 5,292, 646, supra, describes a des-Pro form of IL-11 in which the N-terminal proline of the mature form of IL-11 (amino acids 22–199) has been removed (amino acids 23–199). As is appreciated by one skilled in the art, any form of IL-11, which retains IL-11 activity, is useful according to the present invention.

In addition to recombinant techniques, IL-11 may also be produced by known conventional chemical synthesis. Methods for constructing the polypeptides useful in the present invention by synthetic means are known to those of skill in the art. The synthetically constructed cytokine polypeptide sequences, by virtue of sharing primary, secondary, or tertiary structural and conformational characteristics with the natural cytokine polypeptides are anticipated to possess biological activities in common therewith. Such synthetically constructed cytokine polypeptide sequences or fragments thereof, which duplicate or partially duplicate the functionality thereof may also be used in the method of this invention. Thus, they may be employed as biologically active or immunological substitutes for the natural, purified cytokines useful in the present invention.

Modifications in the protein, peptide or DNA sequences of these cytokines or active fragments thereof may also produce proteins which may be employed in the methods of this invention. Such modified cytokines can be made by one skilled in the art using known techniques. Modifications of interest in the cytokine sequences, e.g., the IL-11 sequence, may include the replacement, insertion or deletion of one or more selected amino acid residues in the coding sequences. Mutagenic techniques for such replacement, insertion or deletion are well known to one skilled in the art. (See, e.g., U.S. Pat. No. 4,518,584.)

Other specific mutations of the sequences of the cytokine polypeptides which may be useful therapeutically as described herein may involve, e.g., the insertion of one or more glycosylation sites. An asparagine-linked glycosylation recognition site can be inserted into the sequence by the deletion, substitution or addition of amino acids into the peptide sequence or nucleotides into the DNA sequence. Such changes may be made at any site of the molecule that is modified by addition of O-linked carbohydrate. Expression of such altered nucleotide or peptide sequences produces variants which may be glycosylated at those sites.

Additional analogs and derivatives of the sequence of the selected cytokine which would be expected to retain or prolong its activity in whole or in part, and which are expected to be useful in the present method, may also be easily made by one of skill in the art. One such modification may be the attachment of polyethylene glycol (PEG) onto existing lysine residues in the cytokine sequence or the insertion of one or more lysine residues or other amino acid residues that can react with PEG or PEG derivatives into the sequence by conventional techniques to enable the attachment of PEG moieties.

Additional analogs of these selected cytokines may also be characterized by allelic variations in the DNA sequences encoding them, or induced variations in the DNA sequences encoding them. It is anticipated that all analogs disclosed in the above-referenced publications, including those characterized by DNA sequences capable of hybridizing to the disclosed cytokine sequences under stringent hybridization conditions or non-stringent conditions (Sambrook et al., Molecular Cloning, A Laboratory Manual, 2d edit., Cold Spring Harbor Laboratory, New York (1989)) will be similarly useful in this invention.

Also considered useful in these methods are fusion molecules, prepared by fusing the sequence or a biologically active fragment of the sequence of one cytokine to another cytokine or proteinaceous therapeutic agent, e.g., IL-11 fused to IL-6 (see, e.g., methods for fusion described in PCT/US91/06186 (WO92/04455), published Mar. 19, 1992). Alternatively, combinations of the cytokines may be administered together according to the method.

Thus, where in the description of the methods of this invention IL-11 is mentioned by name, it is understood by those of skill in the art that IL-11 encompasses the protein produced by the sequences presently disclosed in the art, as well as proteins characterized by the modifications described above yet which retain substantially similar activity in. Standard laboratory tests are utilized to monitor progress of the treatment. Levels of TNF-α in serum or the biologic effects of TNF-α could be followed in a variety of these diseases. Decreased symptomatology could also be used to monitor the effectiveness of treatment as is well known to physicians skilled in the art of treating such disorders.

The present invention thus involves treating patients having disorders such as AIDS, arthritis (rheumatoid arthritis, osteoarthritis, spondyloarthropathies), antibiotic induced diarrheal diseases (*Clostridium difficile*), multiple sclerosis, osteoporosis, gingivitis, peptic ulcer disease, esophagitis, diabetes, retinitis, uveitis, reperfusion injury after myocardial infarction (MI), cerebral vascular accident (CVA), aphthous ulcers (oral), atherosclerosis (plaque rupture), prevention of minor metastases, asthma, preeclampsia, and allergic disorders such as rhinitis, conjunctivitis, and urticaria and involves administering an effective amount of IL-11 in a pharmaceutical carrier. Treatment is preferably prophylactic, but may also be at the onset of symptoms associated with the aforementioned disorders.

Suitable pharmaceutically acceptable carriers facilitate administration of IL-11 and are well known in the art. Exemplary carriers include sterile saline, lactose, sucrose, calcium phosphate, gelatin, dextrin, agar, pectin, peanut oil, olive oil, sesame oil, and water. Additionally, the carrier or diluent includes a time delay material, such as glyceryl monostearate or glyceryl distearate alone or with a wax. In addition, slow release polymer formulations can be used. Suitable sustain-release matrices contain the active ingredient in a mixture with one or more of the following: sodium bentonite, ethylcellulose, stearic acid, calcium stearate, adipic acid, fumaric acid, polyethylene glycol, deacetylated chitin, and cellulose acetate. Suitable preservatives and/or stabilizers may be included.

Alternatively, IL-11 can be combined with other conventional agents useful in alleviating the symptoms associated with the aforementioned disorders, as is readily apparent to one skilled in the art.

A suitable IL-11 formulation comprises, for example, 5 mg IL-11, 3.10 mg histidine and 22.5 mg glycine, e.g., as a lyophilized powder which can be reconstituted with 1 mL sterile water for injection. As is apparent to one skilled in the art, other suitable formulations are equally effective according to the methods of the present invention. Moreover, the IL-11 can be applied topically in formulations to the nasal mucosa or the conjunctiva or oral mucosa as an aqueous drop formulation or mouthwash, respectively. In localized surface reactions, the topical formulation could be used, while in more severe generalized body-wide inflammatory states, the parenteral routes could be employed, subcutaneous or intravenous injection. Suitable doses of IL-11 may be in the range of 1–50 μg/kg SC for multiple daily doses, but for shorter periods of treatment in severe inflammatory states doses may be increased to 50–100 μg/kg SC or IV. In the treatment of the aforementioned disorders, IL-11 can be administered by any suitable route, but certain routes are preferable for certain disorders, e.g., administered systemically, i.e., parenterally. Of the parenteral routes, subcutaneous and intravenous are preferred.

A suitable treatment regimen for patients undergoing treatment, including for example prophylactic treatment, may be determined by the attending physician based upon such factors as the patient's age, sex, weight, and general health. Generally, a suitable dose of cytokine, e.g., IL-11 ranges broadly, preferably between 1 and 100 µg/kg body weight. Another suitable dose may be in the range of about 10 to 50 µg/kg and about 50 µg/kg with a preferable mount of 25 µg IL-11 per kilogram of body weight. If desired, these doses can be adjusted to units. A unit is conventionally described as the concentration of polypeptide which leads to half-maximal stimulation in a suitable assay, e.g., for IL-11, the T1165 assay described in PCT/US90/06803. Doses may be administered daily for between one day and six months, or for as long as is deemed necessary and safe, as is readily ascertained by standard tests by the attending physician, depending upon the nature of the disorder being treated. Where appropriate, the dosages may be adjusted upward or downward, for example, a dosing regimen requiring administration of IL-11 at a dose of 25 µg/kg, daily for one week, or fewer days, or multiple weeks if indicated. The progress if treatment is appropriately monitored by measurement of markers associated with the disorder being treated to determine if such a dose results in a decrease of for example, TNF-α levels (or corresponding marker) and if not, increasing the dose two-fold for an additional time period of treatment and measurement of marker levels until an effective dosing regimen is reached.

The following examples illustrate the methods of the present invention and in particular the use of IL-11 in treating AIDS, arthritis (rheumatoid arthritis, osteoarthritis, spondyloarthropathies), antibiotic induced diarrheal diseases (*Clostridium difficile*), multiple sclerosis, osteoporosis, gingivitis, peptic ulcer disease, esophagitis, diabetes, retinitis, uveitis, reperfusion injury after myocardial infarction (MI), cerebral vascular accident (CVA), aphthous ulcers (oral), atherosclerosis (plaque rupture), prevention of tumor metastases, asthma, and allergic disorders such as rhinitis, conjunctivitis, and urticaria. However, the examples do not limit the scope of the invention in any way.

Example 1 describes the treatment of arthritis (rheumatoid arthritis, osteoarthritis, spondyloarthropathies). Example 2 relates to the treatment of antibiotic induced diarrheal diseases (*Clostridium difficile*); Example 3 describes the treatment of multiple sclerosis; Example 4 relates to the treatment of osteoporosis; and Example 5 describes the treatment of peptic ulcer disease.

EXAMPLE 1

Treatment of Arthritis (Rheumatoid Arthritis, Osteoarthritis, Spondyloarthropathies)

HLA-B27 transgenic Fischer 344 rats spontaneously exhibit lesions of the gastrointestinal system, the joints, the skin and the gonads which appear similar to the spondylarthropies in humans that have been associated with the HLA-B27 and $\beta_2$-microglobulin genes (Hammer et al., Cell 63:1099 (1990)). Overt inflammatory bowel disease is observed in 100% of the rats by 20 weeks of age. Recently, Scofield et al., PNAS 90:9330 (1993) reported that short portions of the primary amino acid sequence of the hypervariable regions of HLA-B27 share homology with the proteins of gram-negative bacteria and that they are capable of binding the HLA-B27 molecule. After birth as the gastrointestinal tract is colonized with bacteria, tolerance to the HLA-B27 molecule is broken as the mucosa is exposed to the luminal bacteria. This results in the development of an autoimmune phenomenon which leads to a chronic, inflammatory syndrome manifest initially in the gastrointestinal tract.

During studies of these rats, administration of rhIL-11 reduced the swelling and redness of tarsal and knee joints of these animals. Blinded assessment of radiographs of the joints of these animals revealed that 4 of 6 vehicle treated animals had radiographic evidence of joint distension and osteophyte formation, while only one of 6 rhIL-11 treated animal had radiographic changes. Subsequent histologic evaluations confirmed the presence of pannus formation, degeneration of the articular cartilage and osteophyte formation in the vehicle treated animals. rhIL-11 treated animals exhibited minimal to no lesions.

EXAMPLE 2

Treatment of Antibiotic Induced Diarrheal Diseases (*Clostridium difficile*)

Toxin A from *C. difficile*, binds to a brush border toxin receptor, causing secretion of fluid, increased intestinal permeability and an intense inflammatory infiltrate in rat ileum. As shown below, pretreatment with rhIL-11 reduces the intestinal effects of toxin A.

Adult rats were injected (SC) with either rhIL-11 (150 µg/kg) or vehicle 20 min before administration of toxin A. Rat ileal loops (5 cm) were then injected with toxin A (5 µg) or buffer (0.4 ml) and 4 hours later, enterotoxicity was assessed by fluid secretion (mg/cm) and blood-to-lumen excretion of $^3$H-marmitol (dpm/loop).

TABLE 1

| Results | Secretion | Permeability |
| --- | --- | --- |
| Buffer (n = 8) | 109 + 6 | 1,450 + 270 |
| Toxin A (n = 12) | 388 + 14** | 45,200 + 4,500** |
| rhIL-11 + Toxin A (n = 5) | 211 + 15++ | 5,460 + 2,030++ | n = number of rats tested, *p < 0.05 and **p < 0.01 vs. Buffer, ++p < 0.01 vs Toxin A Histologic evaluation indicated that rhIL-11 attenuated epithelial damage caused by toxin A, but had no effect on neutrophil infiltration or congestion and edema of the mucosa. Preincubation of rhIL-11 (50 µg/ml) with purified toxin A (5 µg/ml) in vitro did not alter toxin A-induced cell rounding in cultured lung fibroblasts or 3H-toxin A specific binding to rat ileal brush borders.

rhIL-11 significantly inhibits *C. difficile* toxin A-mediated secretion (by 45.6%) and permeability (by 88%) and reduces mucosal damage in vivo, but has no apparent effect on fibroblast rounding or toxin A binding to its membrane receptor in vitro.

EXAMPLE 3

Treatment of Multiple Sclerosis

Experimental autoimmune encephalomyelitis (EAE) is considered the best available animal counterpart for multiple sclerosis (MS) and has thus been widely used to study potential immunoregulatory mechanisms involved in the pathogenesis of this disease. As the T cell subsets, cytokines, and cellular adhesion molecules that mediate successful disease induction have been extensively characterized, the model serves as a valuable tool for delineating the biological actions of immunoregulatory proteins. In susceptible strains of mice, disease can be induced by injection of encephalitogenic proteins (myelin basic protein, (MBP) or proteolipid protein (PLP)) in complete Freund's adjuvant (CFA). Alternatively, EAE can be passively transferred to naive animals with MBP or PLP-sensitized T lymphocytes, encephalitogenic T cell lines, or T cell clones. The clinical course of disease is characterized by weight loss and a progressive paralysis which commonly leads to complete bilateral hind limb paralysis. The paralytic episode coincides with an acute perivascular inflammatory response in the central nervous system (CNS) which is comprised predominantly of infiltrating macrophages and T cells. In most species the disease remits spontaneously with the sequence of recovery being the reverse of that of onset.

Based on the pivotal role for macrophage derived cytokines in EAE and the ability of IL-11 to inhibit RAW cell derived TNF-α production in vitro, the effects of IL-11 administration are evaluated in an adoptive transfer model of EAE. The protocol for adoptive transfer is described in detail previously in Leonard, J. Exp. Med. 181:381 (1995). Briefly, spleen or lymph node cells from PLP immunized mice are cultured in vitro with antigen for 96 hours and subsequently transferred to naive mice. $30 \times 10^6$ PLP stimulated spleen or lymph node cells are used in each experiment. Clinical signs of EAE are graded as follows: 0.5, distal limp tail; 1, complete limp tail; 1.5, limp tail with unsteady gait; 2.0 partial hind limb paralysis; 3.0 complete hind limb paralysis.

Administration of IL-11 (250 µg/kg/day as single SC injections) for the first 10 days following PLP stimulated spleen or lymph node cell transfer dramatically altered the course of EAE with both the incidence, as well as the severity of disease reduced by IL-11 treatment. The mean score for controls, (n=10) is greater than 2.5 whereas for IL-11-treated (n=5), the mean score is less than half of the control.

To determine if IL-11 influences T cell activation/expansion in vitro, LNC from PLP primed mice were stimulated with antigen and IL-11 (500 ng/ml) prior to cell transfer. The addition of IL-11 during antigen stimulation had no effect on the ability of the cells to transfer disease to naive mice.

EXAMPLE 4

Treatment of Osteoporosis

Following estrogen depletion, osteoporosis occurs secondary to increased lytic activity of osteoclasts. The effects of rhIL-11 on murine osteoporosis induced by estrogen depletion were assessed in C57Black Mice following ovariectomy. Animals were ovariectomized, and two weeks later rhIL-11 therapy was commenced at 250 µg/kg SC BID for 7 days. The animals were killed and histologic assessment of osteoclast activity in the tibia was performed using TRAP staining. rhIL-11 decreased TRAP staining as compared to saline treated animals(OVX+saline 5.76+2.63% versus OVX+rhIL-11 2.93+1.24, p<0.0001). Thus, the IL-11 treated animals had fewer osteoclasts and therefore, less potential for bone loss.

EXAMPLE 5

Treatment of Peptic Ulcer Disease

The effects of three different dosages of recombinant human interleukin-11 (rhIL-11), given subcutaneously (SC) either prior to Or subsequent to intracolonic administration of trinitrobenzene sulfonic acid (TNB), were studied in Sprague-Dawley rats. The TNB or control were given in a 40% ethanol solution to 312 anesthetized adult male rats allotted to one of 26 groups (n=12). Control groups were: subcutaneous (SC); saline alone; intrarectal (IR); 40% ethanol alone; TNB alone; 40 % ethanol alone, and SC, rhIL-11 at the highest dosage alone and groups combining TNB with rhIL-11 therapy, testing three dosages (100, 300, and 1,000 µg/kg), given either before or after induction of colitis with TNB. Body weight changes were monitored. Rats were euthanized at 3 days, 7 days, or 14 days after TNB administration. At necropsy, samples were collected to evaluate fecal occult blood, mucosal myeloperoxidase activity and mucosal gross indexes of ulceration. Histopathologic and ultrastructural analyses of the colonic mucosa were performed. The TNB alone elicited a prolonged, severe colitis in treated animals, and the ethanol control group showed a short-lasting, less severe colonic inflammatory response. Colonic ulcer indexes of rhIL-11 treated rats showed a consistent, dose-related reduction in the severity of the TNB-induced colitis, whether the interleukin was given before or after the TNB. This reduction was significant (P<0.05) after administration of the intermediate (300 µg/kg) and highest (1,000 µg/kg) dose levels of rhIL-11, in the groups given rhIL-11 for 7 days after TNB. Myeloperoxidase activity was increased during the TNB-induced colitis and was reduced by rhIL-11 administration (P<0.01). Fecal occult blood loss increased with colitis and paralleled its severity. rhIL-11 enhanced mucus production and decreased the severity of TNB-induced colitis. Thus, given these beneficial effects of IL-11 in this colitis model, IL-11 can be used to ameliorate peptic ulcer disease.

While the present invention has been described in terms of specific methods and compositions, it is understood that variations and modifications will occur to those skilled in the art upon consideration of the present invention.

Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

What is claimed:

1. A method of treating spondyloarthropies, comprising administering a pharmaceutically effective amount of IL-11.

2. The method of claim 2 wherein the amount of IL-11 is between 1 and 100 µg/kg body weight.

* * * * *